United States Patent
Fujimoto et al.

(10) Patent No.: US 11,633,469 B2
(45) Date of Patent: Apr. 25, 2023

(54) REASSORTANT INFLUENZA VIRUS PRODUCTION METHOD

(71) Applicant: The Research Foundation for Microbial Diseases of Osaka University, Suita (JP)

(72) Inventors: Takao Fujimoto, Kanonji (JP); Junji Fujita, Kanonji (JP)

(73) Assignee: The Research Foundation for Microbial Diseases of Osaka University, Suita (JP)

( * ) Notice: Subject to any disclaimer, the term of this patent is extended or adjusted under 35 U.S.C. 154(b) by 917 days.

(21) Appl. No.: 16/316,186

(22) PCT Filed: Jul. 11, 2017

(86) PCT No.: PCT/JP2017/025274
§ 371 (c)(1),
(2) Date: Jan. 8, 2019

(87) PCT Pub. No.: WO2018/012498
PCT Pub. Date: Jan. 18, 2018

(65) Prior Publication Data
US 2021/0338798 A1    Nov. 4, 2021

(30) Foreign Application Priority Data
Jul. 15, 2016 (JP) ............................. JP2016-140366

(51) Int. Cl.
*C12N 7/00* (2006.01)
*A61K 39/145* (2006.01)

(52) U.S. Cl.
CPC .............. *A61K 39/145* (2013.01); *C12N 7/00* (2013.01); *C12N 2760/16151* (2013.01)

(58) Field of Classification Search
None
See application file for complete search history.

(56) References Cited

U.S. PATENT DOCUMENTS

| | | | |
|---|---|---|---|
| 2007/0212682 A1* | 9/2007 | Yu | G01N 33/56983 435/5 |
| 2008/0187546 A1* | 8/2008 | Wasmoen | C12N 7/00 424/159.1 |

(Continued)

FOREIGN PATENT DOCUMENTS

| | | |
|---|---|---|
| JP | 10-503093 A | 3/1998 |
| JP | 2013-531481 A | 8/2013 |

(Continued)

OTHER PUBLICATIONS

Supplementary European Search Report dated Nov. 4, 2019, issued for the European Patent Application No. 17827625.9.

(Continued)

Primary Examiner — M Franco G Salvoza
(74) Attorney, Agent, or Firm — Locke Lord LLP

(57) ABSTRACT

Provided is a method of producing reassortant influenza virus containing an antigenic protein of the first influenza virus strain, the method including the following steps: 1) a step of irradiating the first influenza virus strain with ultraviolet light in such an irradiation dose that the first influenza virus strain has initial infection ability and loses or is reduced in virus growth potential; 2) a step of infecting a host with the first influenza virus strain and the second influenza virus strain; 3) a step of culturing the host infected with the first influenza virus strain and the second influenza virus strain, to obtain culture product; 4) a step of inactivating influenza virus strain having an antigenic protein of the second influenza virus strain in the culture product obtained in the step 3); and 5) a step of collecting reassortant influenza virus after the step 4).

12 Claims, 1 Drawing Sheet

(56) References Cited

U.S. PATENT DOCUMENTS

2010/0098725 A1* 4/2010 Liu .................. A61P 31/16
                                                424/209.1
2014/0274806 A1* 9/2014 O'Hagan .......... A61K 39/145
                                                506/17

FOREIGN PATENT DOCUMENTS

| JP | 2014-506133 | A  | 3/2014  |
|----|-------------|----|---------|
| RU | 2457245     | C1 | 7/2012  |
| WO | 96/15231    | A2 | 5/1996  |
| WO | 2011/145081 | A1 | 11/2011 |
| WO | 2013/087945 | A2 | 6/2013  |
| WO | 2014/195920 | A2 | 12/2014 |

OTHER PUBLICATIONS

Office Action Article 94(3) EPC dated May 10, 2021, issued to the EP application No. 17 827 625.9.

Notification of Reasons for Refusal dated Dec. 7, 2017, issued for the Japanese patent application No. 2017-555411 and English translation thereof.

Decision to Grant a Patent dated Apr. 19, 2018, issued for the Japanese patent application No. 2017-555411and English translation thereof.

International Search Report dated Oct. 3, 2017, issued for PCT/JP2017/025274.

Gabriele Neumann et al., "An improved reverse genetics system for influenza A virus generation and its implications for vaccine production," PNAS vol. 102, Nov. 15, 2005, pp. 16825-16829.

Judith M. Fonville et al., Influenza Virus Reassoilment Is Enhanced by Semi-infectious Particles but Can Be Suppressed by Defective Interfering Particles PLoS Pathogens, Oct. 6, 2015: pp. 1-30. (cited in the ISR and JPOA).

Jerome L. Schulman et al., "Selection and Identification of Influenza Virus Recombinants of Defined Genetic Composition," Journal of Virology, Oct. 1976, vol. 20, No. 1, pp. 248-254. (cited in the JPOA).

Vincent R. Racaniello et al., "Isolation of Influenza C Virus Recombinants," Journal of Virology, Dec. 1979, vol. 32, No. 3, pp. 1006-1014 (cited in the ISR and JPOA).

The 2nd Edition Virus experimentology Detailed exposition, Date of publication Showa 57 Feb. 28, 1982, Maruzen-Publication Company pp. 289-290, 321-323 and English translation thereof, (cited in JPOA).

The 2nd Edition Virus experimentology Detailed exposition,Date of publication Showa 57 Feb. 28, 1982, Maruzen-Publication Company pp. 321-325 and English translation thereof.

* cited by examiner

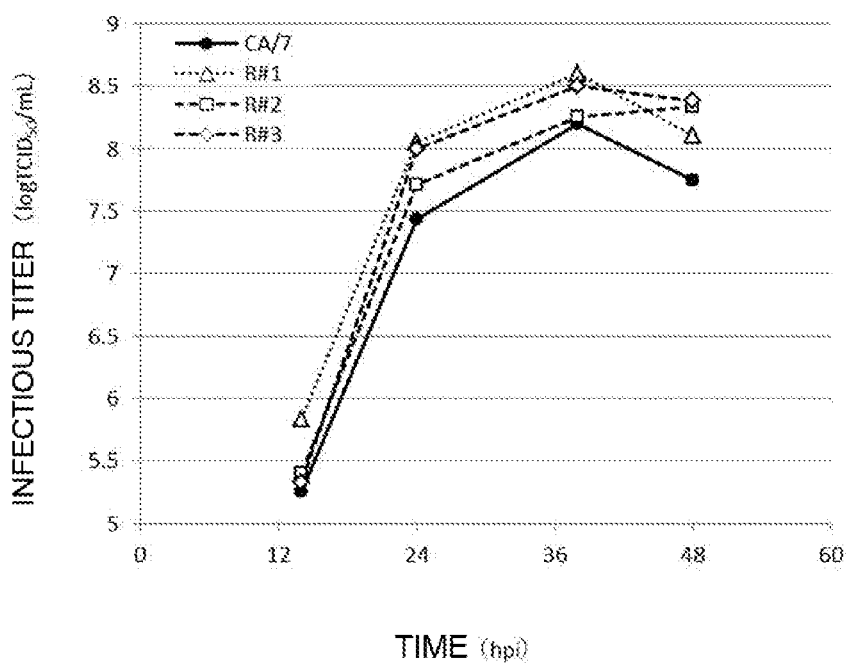

REASSORTANT INFLUENZA VIRUS PRODUCTION METHOD

TECHNICAL FIELD

The present invention relates to reassortant influenza virus production method.

The present application claims priority from Japanese Patent Application No. 2016-140366, which is incorporated herein by reference.

BACKGROUND ART

Influenza is an infectious disease causing epidemics all over the world every year, and is caused by influenza virus. Influenza virus belongs to the family Orthomyxoviridae, and has an envelope having lipid bilayer structure. Influenza viruses are classified into three groups, i.e., type A, type B, and type C, which are referred to as influenza A virus, influenza B virus, and influenza C virus, respectively. Influenza virus generally refers particularly to type A or type B in many cases. Differences between type A, type B, and type C are based on differences in antigenicity of M1 protein and NP protein among proteins constituting virus particles. In addition, even influenza viruses of the same type A or type B are classified into pluralities of subtypes and strains on the basis of differences in antigenicity of hemagglutinin (hereinafter referred to as "HA") and neuraminidase (hereinafter referred to as "NA"), which are molecules on the surface of the envelope.

Influenza virus undergoes an antigenic change with high probability to generate a new type of influenza virus strain. Influenza A virus is classified into 16 kinds of HA (H1 to H16) subtypes and 9 kinds of NA (N1 to N9) subtypes on the basis of the antigenicity of HA and NA thereof. Three kinds of HA (H1, H2, and H3) subtypes of influenza A virus are particularly important pathogens. The H1N1 subtype and H3N2 subtype of influenza A virus spread seasonally and cause human infection. In 2003, influenza virus subtype H5, which is highly lethal and of avian origin, emerged as human pathogen. H1N1 subtype virus emerged as a new type of influenza virus in April 2009, and has spread rapidly among human population. Influenza may even cause a pandemic, and hence there is a demand that influenza vaccine be quantitatively secured.

For manufacture of the influenza vaccine, a method involving growing the influenza virus through utilization of embryonated chicken eggs is used. In addition, manufacturing methods involving growing the influenza virus in cultured cells are beginning to be put into practical use as well. When the embryonated chicken eggs or the cultured cells are utilized for growing the influenza virus, there is a problem in that growth potential of the virus in the host is reduced depending on the subtype or the strain of the influenza virus. Therefore, attempts have been made to produce a recombinant of the influenza virus having improved growth potential in the host by recombination technology. Examples of the recombination technology include reassortment method and reverse genetics method (hereinafter referred to as "RG method"). One example of RG method is a method of producing a recombinant of the influenza virus, involving simultaneously introducing a total of 12 kinds of plasmids, specifically 8 kinds of plasmids (PolI plasmids) for supplying viral RNAs (vRNAs), and 4 kinds of expression plasmids (PolII plasmids) encoding structural proteins needed for forming virus particles, into cells (Non Patent Literature 1). However, RG method places heavy burden on the host cells owing to the simultaneous introduction of several plasmids into the cells. In addition, RG method has a problem in that it takes time to prepare various plasmids, and hence it is difficult to produce the recombinant quickly.

In reassortment method, the host is coinfected with two or more kinds of influenza virus strains, and their genome segments are exchanged and reassorted in growth process to produce a recombinant (Non Patent Literatures 2 to 4). The production of recombinant influenza virus by reassortment method has been performed using chicken eggs as the host. Specifically, an embryonated chicken egg is subjected to mixed infection with backbone virus strain, such as PR8 strain, and circulating strain to produce a recombinant having both a backbone gene of high growth potential and an antigen gene of the circulating strain. However, the reassortment method in which the embryonated chicken eggs are utilized as the host has a problem in that the recombinant of interest cannot always be produced.

For cell-culture influenza vaccine, seed viruses showing high growth potential in cultured cells are desirably used, and efficient production of the seed viruses is needed for stable supply of the vaccine. For the purpose of obtaining a recombinant of the influenza virus, a reassortment method using cultured cells is under consideration. Also in the reassortment method using cultured cells, there is a concern that the recombinant of interest cannot always be produced. In Patent Literature 1, as the reassortment method using cultured cells, there is a disclosure that a host infected with two kinds of influenza virus strains is brought into contact with an inhibitory agent capable of inhibiting transcription or translation of HA and/or NA of a backbone strain, to thereby produce reassortant influenza virus.

CITATION LIST

Patent Literature

[PTL 1] WO 2011/145081 A1

Non Patent Literature

[NPL 1] Neumann et al., PNAS Vol. 102, p. 16825-16829 (1999)
[NPL 2] PLoS Pathog. 2015 October; 11(10): e1005204.
[NPL 3] J Virol. 1976 October; 20(1): 248-54.
[NPL 4] "Special Experimental Virology", second edition, published on Feb. 28, 1982, published by Maruzen Publishing Co., Ltd., p. 321-325

SUMMARY OF INVENTION

Technical Problem

An object of the present invention is to provide a method of producing reassortant influenza virus having genome segments of two or more kinds of influenza virus strains. Another object of the present invention is to provide influenza virus having high growth potential through the use of the method.

Solution to Problem

The inventors of the present invention have made extensive investigations in order to achieve the above-mentioned objects, and as a result, have found that reassortant influenza virus of interest can be produced early and efficiently by: irradiating first influenza virus strain with ultraviolet light to cause its viral replication ability to be lost; and using an antibody that selectively inactivates influenza viruses having an antigenic protein of second influenza virus strain. Thus, the inventors have completed the present invention.

That is, the present invention includes the following.

1. A method of producing reassortant influenza virus containing an antigenic protein of the first influenza virus strain, the method including the following steps:

1) a step of irradiating the first influenza virus strain with ultraviolet light in such an irradiation dose that the first influenza virus strain has initial infection ability and loses or is reduced in virus growth potential;

2) a step of infecting a host with the first influenza virus strain and the second influenza virus strain;

3) a step of culturing the host infected with the first influenza virus strain and the second influenza virus strain, to obtain culture product;

4) a step of inactivating influenza virus having an antigenic protein of the second influenza virus strain in the culture product obtained in the step 3); and 5) a step of collecting reassortant influenza virus after the step 4).

2. A method of producing reassortant influenza virus according to the above-mentioned item 1, wherein the step 4) includes bringing an antibody against the antigenic protein of the second influenza virus strain into contact with the culture product obtained in the step 3).

3. A method of producing reassortant influenza virus according to the above-mentioned item 1, wherein the step 4) includes incubating the culture product obtained in the step 3) with addition of antiserum against the second influenza virus strain.

4. A method of producing reassortant influenza virus according to the above-mentioned item 3, wherein the antiserum has final dilution factor of from 2 times to 1,000 times.

5. A method of producing reassortant influenza virus according to the above-mentioned item 3, wherein the antiserum includes infected serum.

6. A method of producing reassortant influenza virus according to any one of the above-mentioned items 1 to 5, wherein the step 2) includes infecting the host with the first influenza virus strain by bringing the first influenza virus strain into contact with the host at moi of from $1 \times 10^{-6}$ to 10.

7. A method of producing reassortant influenza virus according to any one of the above-mentioned items 1 to 6, wherein the step 2) includes infecting the host with the first influenza virus strain, and then infecting the host with the second influenza virus strain.

8. A method of producing reassortant influenza virus according to any one of the above-mentioned items 1 to 7, wherein the step 5) includes selecting, from reassortant influenza virus, reassortant influenza virus of interest.

9. A method of producing reassortant influenza virus according to any one of the above-mentioned items 1 to 8, wherein the second influenza virus strain includes influenza A virus subtype H1N1 or influenza A virus subtype H3N2.

10. Reassortant influenza virus, which is produced by the method of producing reassortant influenza virus of any one of the above-mentioned items 1 to 9.

11. Reassortant influenza virus according to the above-mentioned item 10, wherein reassortant influenza virus includes an antigenic protein derived from the first influenza virus strain, and a backbone protein of the second influenza virus strain.

12. A method of producing reassortant influenza virus according to any one of the above-mentioned items 1 to 9, wherein the host includes cultured cells.

13. A method of producing reassortant influenza virus according to any one of the above-mentioned items 1 to 9, wherein the host includes an embryonated chicken egg.

Advantageous Effects of Invention

According to the method of producing reassortant influenza virus of the present invention, reassortant influenza virus that is a recombinant can be produced early and efficiently. According to the method of the present invention, influenza virus having high growth potential can be produced early and efficiently.

BRIEF DESCRIPTION OF DRAWINGS

FIG. 1 is a graph for showing the results of confirmation of the growth potentials of the antigenic strain and reassortant influenza viruses of interest in cultured cells (Example 3).

DESCRIPTION OF EMBODIMENTS

The present invention is directed to a method of producing reassortant influenza virus having genome segments of two or more kinds of influenza virus strains.

Influenza virus has an envelope having lipid bilayer structure. The inner layer of the envelope is mainly formed of matrix protein and RNP, which is a complex of RNA and proteins. On the outer layer, influenza NA protein and influenza HA protein, which are so-called surface proteins, are present as protrusions. The influenza virus is formed of eight genome segments, specifically PB2, PB1, PA, HA, NP, NA, M, and NS segments. The HA and NA genome segments encode HA and NA antigenic proteins, respectively, and the other six genome segments, which are the PB2, PB1, PA, NP, M, and NS segments, encode backbone proteins.

As a recombination technology for the influenza virus, there are given RG method and reassortment method. RG method involves simultaneously introducing several plasmids into cells, and hence poses many problems on efficient production of the recombinant virus of interest, such as the selection of cells capable of withstanding the introduction, the preparation of the plasmids, and the compatibility between the plasmids and the cells. Meanwhile, in reassortment method, a host is coinfected with influenza virus strains, and their genome segments are exchanged and reassorted in growth process to produce a recombinant, and hence no plasmid is utilized. Accordingly, reassortment method can significantly reduce the cost and time required for the production of recombinant virus as compared to RG method.

However, the related-art reassortment method has a significant problem in that its recombination efficiency is low. Accordingly, reassortant influenza virus of interest cannot always be obtained. Meanwhile, in Patent Literature 1, there is a description that it takes about 35 days to obtain reassortant influenza virus having high growth potential. That is, although reassortment method can reduce the time and cost required for the production of viruses as compared to the RG method, which requires the preparation of several plasmids, there is a concern that it may take a long period of time to obtain reassortant influenza virus of interest owing to the low recombination efficiency.

The inventors of the present invention have considered that, in the related-art reassortment method, the failure to achieve suitable recombination efficiency is caused by insufficient control of genome segment exchange between influenza viruses grown in coinfected cells and/or insufficient inactivation of unnecessary viruses other than the influenza virus of interest. As a result of their extensive investigations, the inventors have found that reassortant influenza virus can be produced early and efficiently by: irradiating the first influenza virus strain with ultraviolet light to cause its viral replication ability to be lost; and using a neutralizing antibody against antigenic proteins of the second influenza virus strain. Further, the inventors have found that genome segment exchange occurring in the host at the time of viral coinfection can be controlled by irradiating the first influenza virus strain with ultraviolet light in such an irradiation dose that the first influenza virus strain has initial infection ability and loses or is reduced in virus growth potential. Further surprisingly, the inventors have found that, when infected serum is used instead of immune serum which is generally used in the reassortment method, influenza virus having the antigenic proteins of the second influenza virus strain in the culture product can be completely inactivated. In addition, the inventors have found that, according to the production method of the present invention, the recombination efficiency is improved, and hence reassortant influenza virus having high growth potential can be produced early.

Reassortant influenza virus of interest to be obtained in the present invention is one in which at least one of genome segments from the genome encoding HA and NA (preferably at least the genome segment from the genome encoding HA) is derived from the first influenza virus strain and at least one of the other genome segments (preferably at least the genome segment from the genome encoding PB1) is derived from the second influenza virus strain. In the present invention, the first influenza virus strain is sometimes referred to as antigenic strain, and the second influenza virus strain is sometimes referred to as donor strain or backbone strain. Now, each step included in the production method of the present invention is described.

Step 1) A step of irradiating the first influenza virus strain with ultraviolet light in such an irradiation dose that the first influenza virus strain has initial infection ability and loses or is reduced in virus growth potential.

In this step, the first influenza virus strain is irradiated with ultraviolet light so as to be inactivated. The irradiation dose of the ultraviolet light is preferably such that the first influenza virus strain after the ultraviolet light irradiation has initial infection ability for the host, but its virus growth potential after infection is lost or reduced. That the virus growth potential after infection is lost or reduced means that, when the host is infected with the first influenza virus alone, the growth potential of the virus in the host is not confirmed, or the virus growth potential is reduced as compared to that of the first influenza virus strain that has not been subjected to the ultraviolet light irradiation. The virus growth potential may be evaluated by using known index, such as virus infectious titer or Plaque Forming Unit (PFU). In addition, when the host is infected with the first influenza virus strain after the ultraviolet light irradiation, the first influenza virus strain needs to have infection ability for the host, namely the initial infection ability. When the host is cultured cells, a state of having the initial infection ability means that cytopathic effect (CPE) caused by the virus subjected to the ultraviolet light irradiation is observed. In this step, it is preferred that the first influenza virus strain be irradiated with ultraviolet light irradiation dose equivalent to that in the case where ultraviolet light irradiation is performed in the Time Mode of Spectrolinker XL-1000 (Spectronics Corporation) for from 1 second to 60 seconds, preferably from 5 seconds to 50 seconds, still more preferably from 10 seconds to 40 seconds, still more preferably from 10 seconds to 30 seconds. The irradiation conditions, such as the apparatus to be used for such ultraviolet light irradiation (ultraviolet light intensity, distance from light source, and the like are described in Examples below) and the irradiation time, are mere examples, and those conditions may be appropriately adjusted/changed as long as ultraviolet light irradiation dose comparable to that under the irradiation conditions is achieved. The ultraviolet light irradiation dose under the above-mentioned conditions enables influenza virus having initial infection ability for the host but having its virus growth potential lost or reduced to be efficiently obtained, and hence is preferred. In the present invention, by virtue of causing the virus growth potential of the first influenza virus strain to be lost or reduced while having initial infection ability for the host, recombination efficiency in the host can be improved.

Step 2) A step of infecting a host with the first influenza virus strain and the second influenza virus strain.

The host may be infected with the first influenza virus strain and the second influenza virus strain simultaneously or not simultaneously. It is preferred that the host be infected with the first influenza virus strain, and then infected with the second influenza virus strain. The infection of the host with each of the influenza virus strains is performed by bringing the host and the influenza virus strain into contact with each other. The first influenza virus strain is preferably brought into contact with the host at preferably moi of from $1 \times 10^{-6}$ to 10, more preferably moi of from 0.001 to 1, still more preferably moi of from 0.1 to 1. The second influenza virus strain is preferably brought into contact with the host at preferably moi of from 0.001 to 10, more preferably moi of from 0.01 to 1, still more preferably moi of from 0.1 to 1. Hitherto, in order to coinfect a host with influenza viruses, it has been required that the host be infected by bringing the viruses into contact therewith at high concentrations. However, in the present invention, even at low concentrations, the influenza viruses coinfect the host to allow a recombinant to be efficiently produced. The moi of the first influenza virus strain is a value before the irradiation with ultraviolet light. The infectious titer ($TCID_{50}$/mL) of each of the influenza viruses may be confirmed in accordance with the method disclosed in "Part IV" of "Influenza Diagnosis Manual (3rd edition, September 2014)" written by the National Institute of Infectious Diseases, Japan (hereinafter referred to as "Reference 1"), and the moi may be calculated by dividing the infectious titer by the number of cells.

Step 3) A step of culturing the host infected with the first influenza virus strain and the second influenza virus strain, to obtain culture product.

Through the culture of this step, the influenza viruses are reassorted in the host. Culture conditions for the host, such as culture temperature, may be any conditions as long as the conditions allow the influenza viruses to grow in the host. When the host is cultured cells, medium to be used for the culture is preferably liquid medium. Serum of animal origin is often added to liquid medium, but the possibility cannot be denied that the serum of animal origin contains an agent that inhibits the growth of the influenza virus of interest. Therefore, serum-free medium that does not contain the agent is more preferably used. Examples of the serum-free medium include Eagle's MEM medium (Nissui Pharmaceutical), Opti PRO SFM (Thermo Fisher Scientific), VP-SFM (Thermo Fisher Scientific), EX-CELL MDCK (SAFC Biosciences), UltraMDCK (Lonza), ProVero 1 (Lonza), and BalanCD MDCK (Irvine Scientific). Culture time is preferably from about 1 day to about 5 days, more preferably from about 2 days to about 3 days. In this step, the culture product is obtained after the culture. The culture product contains reassortant influenza virus reassorted in the host and influenza virus having the antigenic protein of the second influenza virus strain. The viruses are mainly contained in allantoic fluid in the case where the host is an embryonated chicken egg, and are mainly contained in culture supernatant in the case where the host is cultured cells.

Step 4) A step of selectively inactivating influenza virus having an antigenic protein of the second influenza virus strain in the culture product obtained in the step 3).

The inactivation of the virus may be achieved using a physical technique, a chemical technique, or any other technique, but is preferably achieved by treating the influenza viruses having the antigenic protein of the second influenza virus strain in the culture product by bringing a neutralizing antibody that binds to the antigenic protein into contact therewith.

A virus amount in the culture product to be subjected to this step may be represented by the product of a virus infectious titer ($TCID_{50}$/mL) and dose (mL). As long as the culture product contains reassortant influenza virus of interest, the virus amount may be of any value, but is preferably $10^2$ $TCID_{50}$ or more, more preferably $10^3$ $TCID_{50}$ or more, still more preferably $10^4$ $TCID_{50}$ or more. When the virus amount falls within such range, reassortant virus of interest can be isolated in the step 5). In addition, the virus amount may be appropriately adjusted through dilution or concentration by a known technique.

The neutralizing antibody only needs to be the one that binds to the antigenic protein of the second influenza virus strain and does not bind to the antigenic protein of the first influenza virus strain, and may be a polyclonal antibody or a monoclonal antibody. The neutralizing antibody is preferably a neutralizing antibody that specifically binds to the antigenic protein of the second influenza virus strain. In one embodiment, antiserum containing a neutralizing antibody that specifically binds to the antigenic protein of the second influenza virus strain may be used. Through the addition of the antiserum to the culture product obtained in the step 3), the influenza virus having the antigenic protein of the second influenza virus strain and the neutralizing antibody that specifically binds to the antigenic protein can be brought into contact with each other.

The antiserum against the second influenza virus strain may be immune serum or infected serum, but infected serum is preferably selected. Such antiserum may be prepared by a known technique. The immune serum may be obtained from blood collected from a mammal to which an antigen derived from the second influenza virus strain has been administered. The antiserum is prepared by, for example, immunizing a mammal, such as a rabbit, a goat, a sheep, a mouse, or a rat through the administration of an antigen derived from the second influenza virus strain as an immunogen. As administration means, intraperitoneal injection, intravenous injection, subcutaneous injection, or the like is adopted, and intradermal injection is also adopted in some cases. Booster immunization is repeated several times, and the immune serum may be obtained from blood collected from the mammal 3 days to 10 days after final immunization. In addition, the infected serum may be obtained from blood collected from a mammal infected with the second influenza virus strain. For example, an influenza virus-susceptible mammal, such as a ferret or a mouse, is infected with the second influenza virus strain. As an infection method, a method such as spray inoculation or nasal inoculation is adopted. Blood is collected from the mammal on or after the 10th to 14th day after the infection, and the infected serum may be obtained therefrom.

The obtained antiserum preferably has its neutralizing activity nonspecific to the antigen derived from the second influenza virus strain inactivated by a known technique, such as Receptor Destroying Enzyme (RDE) treatment, trypsin treatment, or potassium periodate treatment. The antiserum is preferably added to the culture product at such a concentration as to give final dilution factor of preferably from 2 times to 1,000 times, more preferably from 4 times to 10 times.

The antibody titer of the neutralizing antibody is preferably measured in advance. The antibody titer may be measured by a known technique, such as particle agglutination method (PA), indirect fluorescent antibody method (IFA), immune adherence hemagglutination method (IAHA), neutralization method (NT), hemagglutination inhibition method (HI), complement fixation method (CF), enzyme immunoassay (EIA), radioimmunoassay (RIA), chemiluminescence immunoassay (CLIA), or latex agglutination turbidimetry (LA). In an embodiment in which the virus infectious titer of the culture product is from $10^7$ $TCID_{50}$/100 μL to $10^8$ $TCID_{50}$/100 μL, antiserum showing antibody titer measured by HI method of 10 or more, preferably 12.8 or more, more preferably 80 or more, still more preferably 128 or more may be used. When the antibody titer falls within such range, the antigenic protein of the second influenza virus strain present in the culture product and the neutralizing antibody suitably bind to each other, and hence the influenza virus having the antigenic protein can be efficiently inactivated.

Subsequently, a mixture of the culture product and the neutralizing antibody is brought into contact with the host, and the infected host is cultured under suitable conditions described in the step 3) to selectively grow reassortant virus of interest. When the host is cultured cells, cytopathic effect (CPE) caused by reassortant virus of interest is confirmed.

Step 5) A step of collecting reassortant influenza virus of interest.

In this step, reassortant influenza virus produced in the step 4) is collected. In this step, reassortant influenza virus of interest may be further selected from the collected reassortant influenza viruses. Reassortant influenza virus of interest may be selected by being isolated by plaque method, followed by analysis of genome segments. Known techniques may be used as plaque method and a method for the analysis of genome segments.

According to the production method of the present invention, reassortant influenza virus of interest can be acquired in a period that is equal to or shorter than half that in the related art. When an existing neutralizing antibody or antiserum can be used, reassortant influenza virus of interest can be acquired in preferably 17 days or less, more preferably 15 days or less, still more preferably 13 days or less, most preferably 10 days or less. When a new antiserum needs to be prepared, reassortant influenza virus of interest can be acquired in preferably 24 days or less, more preferably 20 days or less, still more preferably 16 days or less, most preferably 12 days or less. When vaccine needs to be obtained early at the time of a pandemic or the like, the method of the present invention is extremely useful.

Herein, the ease of production of a recombinant of influenza virus is indicated by recombination efficiency. The recombination efficiency refers to the ratio of the number of clones of plaque that is reassortant influenza virus of interest to the total number of clones isolated as plaques in a reassortant production experiment. The reassortant production experiment means an experiment involving infecting the host with the first influenza virus strain and the second influenza virus strain to produce reassortant influenza virus. According to the production method of the present invention, recombination efficiency of preferably 60% or more, more preferably 80% or more, still more preferably 95% or more, most preferably 100% can be achieved.

The first influenza virus strain or the second influenza virus strain of the present invention is not particularly limited, and may be selected as appropriate for reassortant influenza virus of interest. For example, the first influenza virus strain or the second influenza virus strain may be selected from all currently known subtypes, and subtypes to be isolated and identified in the future. In the case of influenza A virus, influenza viruses including combinations of various HA subtypes and NA subtypes are conceivable. In the case of influenza B virus, influenza viruses including a combination of a Victoria lineage and a Yamagata lineage are conceivable.

Each influenza A virus subtype has high RNA genome variability, and hence new strains are frequently generated. Influenza that is said to have caused a global outbreak after being recognized as causing an outbreak in Mexico in April 2009 is called novel influenza, swine influenza, pandemic influenza A (H1N1), swine flu, A/H1N1 pdm, or the like. Novel influenza, which is said to have spread among humans after its virus, which had caused an outbreak among swine, directly infected humans from swine at farms and the like, is distinguished from influenza A virus subtype H1N1 serving as Russian influenza A (hereinafter referred to as "H1N1 subtype") and influenza A virus subtype H3N2 serving as Hong Kong influenza A (hereinafter referred to as "H3N2 subtype"), which had existed earlier and were seasonal. In addition, because of the high RNA genome variability, even in the same influenza A virus subtype, virus strains are distinguished from each other on the basis of the time and place of isolation.

Other than influenza virus isolated from a living body as described above, the influenza virus strain to be used in the present invention may be recombinant virus produced by adding modifications, such as attenuation, chicken egg growth adaptation, cell culture growth adaptation, modification into temperature-sensitive phenotype, and mucosal administration adaptation, so as to be applicable to influenza vaccine. In addition, as means for adding modifications, there are given, for example: a method involving introducing mutations into eight RNA segments, such as antigen site and polymerase site, of influenza virus; a method involving producing attenuated virus by cold-passage; and a method involving adding mutagen to virus culture system.

A strain which is excellent in growth potential in a desired host is preferably selected as the second influenza virus strain in the present invention. When the host is a chicken egg, the second influenza virus strain is preferably of an H1N1 subtype. An example of H1N1 subtype is A/Puerto Rico/8/34 (H1N1). Meanwhile, when the host is cultured cells, in particular, MDCK cells, the second influenza virus strain is preferably of an H3N2 subtype. Examples of H3N2 subtype include A/Ibaraki/N12232/2012 (H3N2), A/Hiroshima/52/2005 (H3N2), and A/Panama/2007/99 (H3N2). As the first influenza virus strain, a strain having an antigenic protein of interest only needs to be used without any particular limitation. The first influenza virus strain may be a currently isolated and identified strain or a strain to be isolated and identified in the future, and may be influenza A virus or influenza B virus. Specific examples of the first influenza virus strain include, but not limited to, A/California/7/2009 (H1N1) pdm09, A/California/4/2009 (H1N1) pdm09, A/New Caledonia/20/99 (H1N1), A/Solomon Islands/3/2006 (H1N1), A/Brisbane/59/2007 (H1N1), A/Panama/2007/99 (H3N2), A/Wyoming/3/2003 (H3N2), A/New York/55/2004 (H3N2), A/Hiroshima/52/2005 (H3N2), A/Uruguay/716/2007 (H3N2), A/Victoria/210/2009 (H3N2), A/Victoria/361/2011 (H3N2), A/Texas/50/2012 (H3N2), A/New York/39/2012 (H3N2), A/Switzerland/9715293/2013 (H3N2), A/Vietnam/1194/2004 (H5N1), A/Indonesia/5/2005 (H5N1), A/Anhui/1/2005 (H5N1), A/Shanghai/2/2013 (H7N9), A/Anhui/1/2013 (H7N9), B/Shandong/7/97, B/Shanghai/361/2002, B/Malaysia/2506/2004, B/Florida/4/2006, B/Brisbane/60/2008, B/Wisconsin/1/2010, B/Massachusetts/2/2012, B/Phuket/3073/2013, and B/Texas/2/2013.

In addition, reassortant influenza virus of interest produced by the present invention may be used as seed virus for the manufacture of influenza vaccine. For the step of purifying reassortant influenza virus of interest, known techniques or any techniques to be developed in the future may be used.

The host to be used in the production method of the present invention may be an embryonated chicken egg, or may be cultured cells. When the embryonated chicken egg is used as the host, a specific pathogen-free (SPF) embryonated chicken egg may be used.

In the production method of the present invention, when the cultured cells are used as the host, the cultured cells may be any cultured cells that influenza virus can infect to be replicated. The cultured cells are preferably mammalian cells, and examples thereof include, but not limited to, hamster, bovine, primate (including human and monkey), and canine cells. More specific examples thereof include: MDCK cells derived from the Madin-Darby canine kidney; and Vero cells derived from the African green monkey kidney. The MDCK cells in the present invention are more specifically MDCK cells internationally deposited and identified by accession number NITE BP-02014. Such cells were domestically deposited to NITE Patent Microorganisms Depositary at the Biological Resource Center (2-5-8 Kazusakamatari, Kisarazu-shi, Chiba, Japan, postal code: 292-0818) with accession number NITE P-02014 on Mar. 4, 2015, and then a request for conversion to an international deposit under the Budapest Treaty was made to NITE Patent Microorganisms Depositary at the Biological Resource Center.

EXAMPLES

To help understanding of the present invention, the present invention is specifically described below by way of Examples and Reference Examples, but the present invention is not limited to Examples and Reference Examples.

(Reference Example 1) Production of Reassortant Influenza Virus Using Live Viruses Reassortant influenza virus was produced by using live viruses without subjecting an antigenic strain to ultraviolet light irradiation (hereinafter referred to as UV irradiation).

1. Used Virus Strains and Used Antiserum

First influenza virus strain (antigenic strain): A/California/7/2009 (H1N1) pdm09 (hereinafter referred to as "CA/7")

Second influenza virus strain (donor strain): A/Ibaraki/N12232/2012 (H3N2) (hereinafter referred to as "IB/232")

Anti-donor strain serum: RDE-treated infected serum (HI antibody titer: 1,280) of ferret with the donor strain, having final dilution factor of 2 times 2. Production of Reassortant Influenza Virus 1) Influenza virus solutions of the donor strain and the antigenic strain were prepared using Eagle's MEM medium containing glutamine (4 mM), glucose (4.6 g/L), sodium hydrogen carbonate (20 mM), and 0.1×TrypLE Select (hereinafter referred to as "medium for virus culture"). The influenza virus solution of the donor strain is hereinafter referred to as "donor strain solution", and each influenza virus solution of the antigenic strain is referred to as "antigenic strain solution". $10^5$ $TCID_{50}$/mL donor strain solution, and $10^4$ $TCID_{50}$/mL, $10^3$ $TCID_{50}$/mL, $10^2$ $TCID_{50}$/mL and $10^1$ $TCID_{50}$/mL antigenic strain solutions were each prepared using the medium for virus culture. The influenza virus infectious titer ($TCID_{50}$/mL) was confirmed in accordance with the method disclosed in Reference 1.

2) MDCK cells (MDCK cells internationally deposited and identified by accession number NITE BP-02014) were cultured in a 25 $cm^2$ flask to confluence (about $5\times10^6$ cells/flask). After that, the medium was changed to 10 mL of the medium for virus culture, and the cells were simultaneously inoculated with 100 μL of the donor strain solution and 100 μL of each of the antigenic strain solutions having various concentrations.

3) The cells were cultured at 34° C. and 5% $CO_2$ for 2 days.

4) 100 μL of the resultant culture product was mixed with 100 μL of the anti-donor strain serum, and the mixture was incubated at 34° C. for 1 hour.

5) MDCK cells were cultured in a fresh 25 $cm^2$ flask, the medium was changed to 10 mL of the medium for virus culture, and the cells were inoculated with the whole amount of 200 μL of the culture liquid treated with the anti-donor strain serum in 4) above.

6) The cells were cultured at 34° C. and 5% $CO_2$ for 2 days.

7) For 100 μL of the resultant culture product, the operations of 4) to 6) above were repeated again.

8) The resultant culture product was centrifuged (9,000 rpm, 5 minutes), and the supernatant was collected.

9) The centrifuged supernatant was diluted with the medium for virus culture to $10^3$ times, $10^4$ times, $10^5$ times, $10^6$ times, $10^7$ times, or $10^8$ times, and 6-well plates in which MDCK cells had been cultured to confluence were inoculated therewith at 100 μL/well. Two plates were inoculated.

10) The cells were cultured at 34° C. and 5% $CO_2$ for 30 minutes.

11) 0.8% agarose-containing MEM medium (containing glutamine (4 mM) and 0.1×TrypLE Select) was overlaid at 3 mL/well by the same method as in plaque assay. After drying in a safety cabinet, culture in an incubator was started.

12) The cells were cultured at 34° C. and 5% $CO_2$ for 3 days.

13) 1.0% agarose-containing MEM medium (containing neutral red) was overlaid at 2 mL/well, followed by drying in a safety cabinet.

14) MDCK cells were cultured in a fresh 6-well plate, the medium was changed to 2 mL/well of the medium for virus culture, and plaques were isolated for each well. Pickup was performed using an end-cut filter tip.

15) The cells were cultured at 34° C. and 5% $CO_2$ for 3 days.

16) The culture liquid of the isolated plaque was centrifuged (9,000 rpm, 5 minutes), and the supernatant was stored at −80° C.

3. Genetic Analysis

RNA was extracted from the culture supernatant of the plaque isolated in the section 2., and was reverse transcribed to synthesize cDNA, and all genome segments of the viruses were amplified by PCR in accordance with conventional methods, followed by simple purification. The resultant was used as a specimen and subjected to gene sequence analysis to determine which of the donor strain and the antigenic strain each genome segment was derived.

The genetic analysis results of the plaques obtained under the condition of the infection with $10^2$ $TCID_{50}$/mL or $10^4$ $TCID_{50}$/mL of the antigenic strain are shown in Table 1 below. Under the condition of the infection with $10^1$ $TCID_{50}$/mL of the antigenic strain, CPE was not observed in the cells after 2.6) above, and hence the subsequent operations were not performed.

TABLE 1

| Donor | Antigen | Plaque | PB2 | PB1 | PA | HA | NP | NA | M | NS |
|---|---|---|---|---|---|---|---|---|---|---|
| IB/232 | CA/7 | 1 | C | C | C | C | C | C | C | C |
| $10^5$ $TCID_{50}$/mL | $10^2$ $TCID_{50}$/mL | 2 | C | C | C | C | C | C | C | C |
| 100 μL | 100 μL | 3 | C | C | C | C | C | C | C | C |
| | | 4 | C | C | C | C | C | C | C | C |
| | | 5 | C | C | C | C | C | C | C | C |
| | | 6 | C | C | C | C | C | C | C | C |
| | | 7 | C | I | C | C | C | C | C | C |
| | | 8 | C | C | C | C | C | C | C | C |
| | | 9 | C | C | C | C | C | C | C | C |
| | | 10 | C | C | C | C | C | C | C | C |
| | | 11 | C | C | C | C | C | C | C | C |
| | | 12 | C | C | C | C | C | C | C | C |
| IB/232 | CA/7 | 1 | C | C | C | C | C | C | C | C |
| $10^5$ $TCID_{50}$/mL | $10^4$ $TCID_{50}$/mL | 2 | C | C | C | C | C | C | C | C |
| 100 μL | 100 μL | 3 | C | C | C | C | C | C | C | C |
| | | 4 | C | C | C | C | C | C | C | C |
| | | 5 | C | C | C | C | C | C | C | C |
| | | 6 | C | C | C | C | C | C | C | C |
| | | 7 | C | C | C | C | C | C | C | C |
| | | 8 | C | C | C | C | C | C | C | C |
| | | 9 | C | C | C | C | C | C | C | C |
| | | 10 | C | C | C | C | C | C | C | C |
| | | 11 | C | C | C | C | C | C | C | C |
| | | 12 | C | I | C | C | C | C | C | C |

In the table, "I" means being derived from IB/232 (donor strain), and "C" means being derived from CA/7 (antigenic strain).

In most of the analyzed plaques, all the genome segments were derived from CA/7. The 7th plaque under the condition of the infection with $10^2$ TCID$_{50}$/mL of the antigenic strain and the 12th plaque under the condition of the infection with $10^4$ TCID$_{50}$/mL of the antigenic strain were each reassortant influenza virus in which only PB1 segment was derived from IB/232. Under both conditions, the recombination efficiency was less than 10%. In addition, it took a period of about 12 days to acquire the plaques isolated by the technique of section 2. It was considered from those results that the virus amount was important for the mixed infection of the host cells with the donor strain and the antigenic strain. In addition, in the case of the infection with $10^1$ $TCID_{50}$/mL of the antigenic strain, CPE was not observed even on the 5th day of the culture in 2.6) above, and hence virus growth did not occur. Accordingly, it was considered that the donor strain was sufficiently suppressed by being neutralized once with the antiserum.

(Reference Example 2) Confirmation of Influence of Virus Amount of Antigenic Strain on Production of Reassortant Influenza Virus In this Reference Example, the influence of the virus amount of the antigenic strain on the recombination efficiency was investigated. The used viruses and the used antiserum are the same as those of Reference Example 1.

1. Production of Reassortant Influenza Virus

1) With the use of the medium for virus culture, $10^7$ $TCID_{50}$/mL donor strain solution was prepared, and $10^2$ $TCID_{50}$/mL and $10^7$ $TCID_{50}$/mL antigenic strain solutions were each prepared.

2) MDCK cells (MDCK cells internationally deposited and identified by accession number NITE BP-02014) were cultured in a 25 $cm^2$ flask to confluence (about $5\times10^6$ cells/flask), the medium was removed, and the cells were inoculated with 200 μL of the antigenic strain solution, followed by culture at 34° C. and 5% $CO_2$ for 1 hour. After that, the resultant was inoculated with 200 μL of the donor strain solution, and the medium for virus culture was added to a total amount of 10 mL.

3) The cells were cultured at 34° C. and 5% $CO_2$ for 2 days.

4) 100 μL of the resultant culture product was mixed with 100 μL of the anti-donor strain serum, and the mixture was incubated at 34° C. for 1 hour.

5) MDCK cells were cultured in a fresh 25 $cm^2$ flask, the medium was changed to 10 mL of the medium for virus culture, and the cells were inoculated with the whole amount of 200 μL of the culture product treated with the anti-donor strain serum in 4) above.

6) The cells were cultured at 34° C. and 5% $CO_2$ for 2 days.

7) Thereafter, plaques were isolated in the same manner as in 2.8) to 16) of Reference Example 1.

In addition, the plaques isolated in the section 1. were subjected to genetic analysis in the same manner as in Reference Example 1.

The genetic analysis results of the plaques obtained are shown in Table 2 below.

TABLE 2

| Donor | Antigen | Plaque | PB2 | PB1 | PA | HA | NP | NA | M | NS |
|---|---|---|---|---|---|---|---|---|---|---|
| IB/232 | CA/7 | 1 | C | C | C | C | C | C | C | C |
| $10^7$ $TCID_{50}$/mL | $10^2$ $TCID_{50}$/mL | 2 | C | C | C | C | C | C | C | C |
| 200 μL | 200 μL | 3 | C | C | C | C | C | C | C | C |
| | | 4 | C | C | C | C | C | C | C | C |
| | | 5 | C | C | C | C | C | C | C | C |
| | | 6 | C | C | C | C | C | C | C | C |
| | | 7 | C | C | C | C | C | C | C | C |
| | | 8 | C | C | C | C | C | C | C | C |
| | | 9 | C | C | C | C | C | C | C | C |
| | | 10 | C | C | C | C | C | C | C | C |
| IB/232 | CA/7 | 1 | C | C | C | C | C | C | C | C |
| $10^7$ $TCID_{50}$/mL | $10^7$ $TCID_{50}$/mL | 2 | C | C | C | C | C | C | C | C |
| 200 μL | 200 μL | 3 | C | C | C | C | C | C | C | C |
| | | 4 | C | I/C | C | C | C | C | C | C |
| | | 5 | C | I | C | C | C | C | C | C |
| | | 6 | C | I/C | C | C | C | C | C | C |
| | | 7 | C | C | C | C | C | C | C | C |
| | | 8 | C | I/C | C | C | C | C | C | C |
| | | 9 | C | C | C | C | C | C | C | C |
| | | 10 | C | I | C | C | C | C | C | C |

In the table, "I" means being derived from IB/232 (donor strain), and "C" means being derived from CA/7 (antigenic strain).

In the case of the infection with $10^2$ $TCID_{50}$/mL of the antigenic strain, all the genome segments of the analyzed plaques were derived from CA/7. Meanwhile, in each of the 5th and 10th plaques in the case of the infection with $10^2$ $TCID_{50}$/mL of the antigenic strain, PB1 segment was derived from IB/232, and hence it was confirmed that reassortant influenza virus was produced. The 4th, 6th, and 8th plaques had not been able to be isolated into single plaques, and hence PB1 segment was a mixture of IB/232-derived one and CA/7-derived one, but the production of reassortant influenza viruses was confirmed in part of the plaques. It was confirmed that, when the antigenic strain was used at high concentration, the recombination efficiency was improved to about 40%, and hence reassortant influenza virus was easily produced. It took a period of about 10 days to acquire the plaques. In addition, it was suggested that it was difficult to suppress the growth of the antigenic strain in mixed infection between live viruses.

(Example 1) Investigation of UV Irradiation Conditions for Virus Strain

In view of the results of Reference Example 2, in order to use inactivated virus as the first influenza virus strain (antigenic strain), UV inactivation conditions for the antigenic strain were investigated. CA/7 was used as the influenza virus strain.

1. UV Irradiation Experiment

1) $10^6$ $TCID_{50}$/mL of CA/7 was prepared, and dispensed into 3.5 cm dishes at 2 mL each.
2) The dishes of 1) were placed in Spectrolinker XL-1000 (Spectronics Corporation, UV tubes: 254 nm, 8 W×5 tubes), the lids of the dishes were removed, and UV irradiation was performed for from 0 seconds to 120 seconds.
3) The infectious titer of each dish was measured in accordance with conventional method.

The results of the infectious titer measurement are shown in Table 3.

TABLE 3

| | UV irradiation time (seconds) | | | | |
|---|---|---|---|---|---|
| | 0 | 10 | 30 | 60 | 120 |
| Infectious titer [$Log_{10}TCID_{50}$/mL] | 6.00 | <1 | <1 | <1 | <1 |

Through the UV irradiation treatment, the infectious titer of the virus of the antigenic strain can be suppressed to below the detection limit. It is considered that shorter UV irradiation time is preferred for maintaining the initial infection ability of the antigenic strain for the host cells. When the UV irradiation is performed for 10 seconds, the irradiation dose is from about 500 J/m2 to about 1,000 J/m2.

(Example 2) Production of Reassortant Influenza Virus

Recombination efficiency in the case where the antigenic strain was subjected to UV inactivation treatment to suppress the growth of the antigenic strain at the time of mixed infection was confirmed.

1. Used Viruses and Used Antiserum

First influenza virus strain (antigenic strain): CA/7 or A/New Caledonia/20/99 (H1N1) (hereinafter referred to as "NC/20")

Second influenza virus strain (donor strain): IB/232

Anti-donor strain serum is the same as that of Reference Example 1.

2. Production of Reassortant Influenza Virus

1) With the use of the medium for virus culture, $10^7$ $TCID_{50}$/mL donor strain solution and $10^7$ $TCID_{50}$/mL antigenic strain solution were prepared in the same manner as in Reference Example 1.
2) The antigenic strain was subjected to UV irradiation for 10 seconds using Spectrolinker XL-1000 by the same technique as in Example 1.
3) MDCK cells (MDCK cells internationally deposited and identified by accession number NITE BP-02014) were cultured in a 25 cm$^2$ flask to confluence (about 5×10$^6$ cells/flask), the medium was removed, and the cells were inoculated with 200 µL of the antigenic strain solution, followed by culture at 34° C. and 5% $CO_2$ for 1 hour. After that, the resultant was inoculated with 200 µL of the donor strain solution, and the medium for virus culture was added to a total amount of 10 mL.
4) The cells were cultured at 34° C. and 5% $CO_2$ for 2 days.
5) 100 µL of the culture product obtained in 4) above was mixed with 100 µL of the anti-donor strain serum, and the mixture was incubated at 34° C. for 1 hour.
6) MDCK cells (MDCK cells internationally deposited and identified by accession number NITE BP-02014) were cultured in a fresh 25 cm$^2$ flask, the medium was changed to 10 mL of the medium for virus culture, and the cells were inoculated with the whole amount of 200 µL of the culture product treated with the anti-donor strain serum in 5) above.
7) The cells were cultured at 34° C. and 5% $CO_2$ for 2 days.
8) Part of the resultant culture product was centrifuged (9,000 rpm, 5 minutes), and the supernatant was collected.
9) The centrifuged supernatant was diluted with the medium for virus culture to $10^2$ times, $10^3$ times, $10^4$ times, $10^5$ times, $10^6$ times, or $10^7$ times, and 6-well plates in which MDCK cells had been cultured to confluence were inoculated therewith at 100 µL/well. Two plates were inoculated.
10) Thereafter, plaques were isolated in the same manner as in 2.10) to 16) of Reference Example 1.

In addition, the plaques isolated in the section 2. were subjected to genetic analysis in the same manner as in Reference Example 1.

The genetic analysis results of the plaques obtained are shown in Table 4 below.

TABLE 4

| Donor | Antigen | Plaque | PB2 | PB1 | PA | HA | NP | NA | M | NS |
|---|---|---|---|---|---|---|---|---|---|---|
| IB/232 | CA/7 | 1 | I | I | I | C | I | C | C | I |
| $10^7$ $TCID_{50}$/mL | $10^7$ $TCID_{50}$/mL | 2 | I | I | I | C | I | C | C | I |
| 200 µL | 200 µL | 3 | I | I | I | C | I | C | I | I |
| | | 4 | I | I | I | C | I | C | I | I |
| | | 5 | I | I | I | C | I | C | I | I |
| | | 6 | I | I | I | C | I | C | I | I |
| | | 7 | I | I | I | C | I | C | I | I |
| | | 8 | I | I | I | C | I | C | C | I |
| | | 9 | I | I | I | C | I | C | I | I |
| | | 10 | I | I | I | C | I | C | C | I |
| IB/232 | NC/20 | 1 | I | I | I | N | I | N | I | I |
| $10^7$ $TCID_{50}$/mL | $10^7$ $TCID_{50}$/mL | 2 | I | I | I | N | I | N | I | I |
| 200 µL | 200 µL | 3 | I | I | I | N | I | N | I | I |
| | | 4 | I | I | I | N | I | N | I | I |
| | | 5 | I | I | I | N | I | N | I | I |
| | | 6 | I | I | I | N | I | N | I | I |
| | | 7 | I | I | I | N | I | N | I | I |
| | | 8 | I | I | I | N | I/N | N | I/N | N |
| | | 9 | I | I | I | N | N | N | I | I |
| | | 10 | I | I | I | N | I | N | I | I |

In the table, "I" means being derived from IB/232 (donor strain), "C" means being derived from CA/7 (antigenic strain), and "N" means being derived from NC/20 (antigenic strain).

All the analyzed plaques were confirmed to be reassortant influenza viruses. Most of reassortant influenza viruses were reassortant influenza viruses in which the ratio between donor strain-derived segments and antigenic strain-derived segments was 6:2 or 5:3. In the case of the mixed infection with IB/232 and CA/7, the 5:3 reassortant influenza virus had several plaques in which M segment was derived from CA/7. In addition, the 8th plaque in the case where the antigenic strain was NC/20 had not been able to be isolated as a single plaque, and hence the NP segment and the M segment were each a mixture of an IB/232-derived one and an NC/20-derived one. However, according to the analysis results of the plaques, PB2 segment, PB1 segment, and PA segment were solely derived from IB/232, and HA segment, NA segment, and NS segment were solely derived from NC/20, and hence it was suggested that the simultaneously isolated plaques were each reassortant influenza virus. When the UV inactivation treatment of the antigenic strain was performed under the optimal conditions, the recombination efficiency was improved to 100%. In addition, it took a period of from about 9 days to about 10 days to acquire the plaques.

(Example 3) Confirmation of Growth Potential of Reassortant Influenza Virus

MDCK cells (MDCK cells internationally deposited and identified by accession number NITE BP-02014) were infected with produced reassortant influenza viruses and cultured to confirm growth potential. The donor strain used for producing reassortant influenza virus is IB/232, and the antigenic strain is CA/7. The cells were cultured at 34° C. and 5% $CO_2$ for 2 days using the medium for virus culture of Reference Example 1. The infectious titer of the virus culture supernatant was measured in accordance with the method disclosed in Reference 1 to confirm virus growth potential. The genetic analysis results of three kinds of reassortant influenza viruses R #1 to R #3 used are shown in Table 5 below.

TABLE 5

| Segment | Virus | | | |
|---|---|---|---|---|
| | CA/7 | R#1 | R#2 | R#3 |
| PB2 | C | C | I | I |
| PB1 | C | I | I | I |

TABLE 5-continued

| Segment | Virus | | | |
|---|---|---|---|---|
| | CA/7 | R#1 | R#2 | R#3 |
| PA | C | C | I | I |
| HA | C | C | C | C |
| NP | C | C | I | I |
| NA | C | C | C | C |
| M | C | C | C | I |
| NS | C | C | I | I |

In the table, "I" means being derived from IB/232 (donor strain), and "C" means being derived from CA/7 (antigenic strain).

The results are shown in FIG. 1. As compared to the original antigenic strain CA/7, reassortant influenza viruses R #1 to R #3 each showed high infectious titer. Thus, it was suggested that R #1 to R #3 each had high growth potential in MDCK cells as compared to CA/7.

(Example 4) Variation in Recombination Efficiency Based on Antibody Titer

An antibody titer capable of selectively inactivating influenza virus strain having the antigenic protein of the second influenza virus strain (donor strain) was investigated.

1. Used Viruses and Used Antiserum

First influenza virus strain (antigenic strain): CA/7

Second influenza virus strain (donor strain): IB/232

Anti-donor strain serum: RDE-treated infected serum (HI antibody titer: 1,280) of ferret with the donor strain, having initial dilution factor of 2 times 2. Production of Reassortant Influenza Virus 1) Culture product was obtained by the same method as in 2.1) to 4) of Example 2.

2) Infectious titer measurement was performed using part of the culture product.

3) 100 μL of each of anti-donor strain sera diluted with physiological saline so as to have final dilution factors of 10 times, $10^2$ times, $10^3$ times, and $10^4$ times was mixed with 100 μL of the culture product, and the mixture was incubated at 34° C. for 1 hour.

4) The production of reassortant influenza virus was continued by the same method as in 2.6) to 9) of Example 2, and plaques were isolated.

In addition, the plaques isolated in the section 2. were subjected to genetic analysis in the same manner as in Reference Example 1.

The genetic analysis results of the plaques obtained are shown in Table 6 below.

TABLE 6

| # | Dilution factor of mixed culture liquid | Virus content of mixed culture liquid | Dilution factor of serum | HI antibody titer of serum | Plaque | PB2 | PB1 | PA | HA | NP | NA | M | NS |
|---|---|---|---|---|---|---|---|---|---|---|---|---|---|
| 1 | 1 time | $10^{7.57}$ $TCID_{50}$ | 10 times | 128 | 1 | I | I | I | C | I | C | C | I |
| | | | | | 2 | I | I | I | C | I | C | C | I |
| | | | | | 3 | I | I | C | C | I | C | C | C |
| | | | | | 4 | I | I | I | C | I | C | I | I |
| | | | | | 5 | I | I | I | C | I | C | C | I |
| 2 | | | $10^2$ times | 12.8 | 1 | I | I | I | I | I | I | C | I |
| | | | | | 2 | I | I | I | I | I | I | I | C |
| | | | | | 3 | I | I | I | I | I | C | I | I |

TABLE 6-continued

| # | Dilution factor of mixed culture liquid | Virus content of mixed culture liquid | Dilution factor of serum | HI antibody titer of serum | Plaque | PB2 | PB1 | PA | HA | NP | NA | M | NS |
|---|---|---|---|---|---|---|---|---|---|---|---|---|---|
|   |   |   |   |   | 4 | I | I | I | I | C | I | C | I |
|   |   |   |   |   | 5 | I | I | C | I | I | I | I | C |
| 3 |   |   | $10^3$ times | 1.28 | 1 | I | I | I | I | I | I | I | I |
|   |   |   |   |   | 2 | I | I | I | I | I | I | I | I |
|   |   |   |   |   | 3 | I | I | I | I | I | I | I | C |
|   |   |   |   |   | 4 | I | I | I | I | I | I | I | C |
|   |   |   |   |   | 5 | I | I | I | I | I | I | I | C |
| 4 |   |   | $10^4$ times | 0.128 | 1 | I | I | I | I | I | I | I | I |
|   |   |   |   |   | 2 | I | I | I | I | I | I | I | C |
|   |   |   |   |   | 3 | C | I | I | I | I | I | C | I |
|   |   |   |   |   | 4 | I | I | I | I | I | I | C | I |
|   |   |   |   |   | 5 | I | I | I | I | C | I | I | C |

In the table, "I" means being derived from IB/232 (donor strain), and "C" means being derived from CA/7 (antigenic strain).

The infectious titer of the culture product was $10^{7.57}$ TCID$_{50}$/100 μL. When the culture product was treated with anti-donor strain serum having HI antibody titer of 128 or more, all the analyzed plaques were reassortant influenza viruses. Meanwhile, when the culture product was treated with anti-donor strain serum having HI antibody titer of 12.8 or less, HA segment and NA segment were mostly derived from the donor strain, and it was confirmed that influenza virus strain having the antigenic protein of the donor strain was not able to be selectively inactivated.

(Example 5) Allowable Lower Limit Value of Virus Amount of Culture Product

The virus amount of the culture product required for the production of reassortant influenza virus of interest was investigated.

1. Used Viruses and Used Antiserum
First influenza virus strain (antigenic strain): CA/7
Second influenza virus strain (donor strain): IB/232
Anti-donor strain serum: RDE-treated infected serum (HI antibody titer: 1,280) of ferret with the donor strain, having final dilution factor of 2 times 2. Production of Reassortant Influenza Virus
1) Culture product was obtained by the same method as in 2.1) to 4) of Example 2.
2) Infectious titer measurement was performed using part of the culture product.
3) 100 μL of the culture product diluted with the medium for virus culture to 10 times, $10^2$ times, $10^3$ times, $10^4$ times, $10^5$ times, $10^6$ times, $10^7$ times, or $10^8$ times was mixed with 100 μL of the anti-donor strain serum, and the mixture was incubated at 34° C. for 1 hour.
4) The production of reassortant influenza virus was continued by the same method as in 2.6) to 9) of Example 2, and plaques were isolated. However, under the condition that the culture product was diluted to $10^4$ times or more, no plaque was formed, and the subsequent operations were not performed.

In addition, the plaques isolated in the section 2. were subjected to genetic analysis in the same manner as in Reference Example 1.

The genetic analysis results of the plaques obtained are shown in Table 7 below.

TABLE 7

| # | Dilution factor of mixed culture liquid | Virus content of mixed culture liquid | Dilution factor of serum | HI antibody titer of serum | Plaque | PB2 | PB1 | PA | HA | NP | NA | M | NS |
|---|---|---|---|---|---|---|---|---|---|---|---|---|---|
| 1 | 10 times | $10^{6.57}$ TCID$_{50}$ | 2 times | 640 | 1 | I | I | I | C | I | C | I | C |
|   |   |   |   |   | 2 | I | I | I | C | I | C | C | I/C |
|   |   |   |   |   | 3 | I | I | I | C | I | C | C | I |
|   |   |   |   |   | 4 | I | I | I | C | I | C | C | I |
|   |   |   |   |   | 5 | I | I | I | C | I | C | C | I |
| 2 | $10^2$ times | $10^{5.57}$ TCID$_{50}$ |   |   | 1 | I | I | C | C | I | C | C | C |
|   |   |   |   |   | 2 | I | I | I | C | I | C | I | I |
|   |   |   |   |   | 3 | I | I | C | C | I | C | C | C |
|   |   |   |   |   | 4 | I | I | C | C | I | C | C | C |
|   |   |   |   |   | 5 | I | I | C | C | I | C | C | C |
| 3 | $10^3$ times | $10^{4.57}$ TCID$_{50}$ |   |   | 1 | I | C | I | C | I | C | I | C |
|   |   |   |   |   | 2 | I | C | I | C | I | C | I | C |
|   |   |   |   |   | 3 | I | C | I | C | I | C | I | C |
|   |   |   |   |   | 4 | I | C | I | C | I | C | I | C |
|   |   |   |   |   | 5 | I | C | I | C | I | C | I | C |
| 4 | $10^4$ times | $10^{3.57}$ TCID$_{50}$ |   |   | — | No plaque formation | | | | | | | |
| 5 | $10^5$ times | $10^{2.57}$ TCID$_{50}$ |   |   | — | No plaque formation | | | | | | | |

TABLE 7-continued

| # | Dilution factor of mixed culture liquid | Virus content of mixed culture liquid | Dilution factor of serum | HI antibody titer of serum | Plaque | PB2 | PB1 | PA | HA | NP | NA | M | NS |
|---|---|---|---|---|---|---|---|---|---|---|---|---|---|
| 6 | $10^6$ times | $10^{1.57}$ $TCID_{50}$ | | | — | No plaque formation | | | | | | | |
| 7 | $10^7$ times | $10^{0.57}$ $TCID_{50}$ | | | — | No plaque formation | | | | | | | |
| 8 | $10^8$ times | $10^{-1.57}$ $TCID_{50}$ | | | — | No plaque formation | | | | | | | |

In the table, "I" means being derived from IB/232 (donor strain), and "C" means being derived from CA/7 (antigenic strain).

The infectious titer of the undiluted culture product was $10^{7.57}$ $TCID_{50}$/100 µL. When the virus amount in the culture product was $10^{4.57}$ $TCID_{50}$ or more, plaque formation was confirmed. Meanwhile, when the virus amount in the culture product was $10^{3.57}$ $TCID_{50}$ or less, plaque formation was not confirmed. In the conditions under which plaques were formed, all of the analyzed plaques were reassortant influenza viruses.

INDUSTRIAL APPLICABILITY

As described in detail above, according to the method of producing reassortant influenza virus of the present invention, reassortant influenza virus that is recombinant can be produced early and efficiently. According to the method of the present invention, influenza viruses showing high growth potential can be produced early and efficiently, and hence seed virus for the manufacture of influenza vaccine can be quickly produced.

The invention claimed is:

1. A method of producing reassortant influenza virus containing an antigenic protein of a first influenza virus strain, the method comprising the following steps:
   a) irradiating the first influenza virus strain with ultraviolet light with such an irradiation dose that the first influenza virus strain has initial infection ability and loses or is reduced in virus growth potential;
   b) infecting a host cell with the first influenza virus strain and a second influenza virus strain;
   c) culturing the host cell infected with the first influenza virus strain and the second influenza virus strain, to obtain culture product;
   d) bringing a neutralizing antibody that binds to an antigenic protein of the second influenza virus strain into contact with the culture product obtained in step c); and
   e) collecting reassortant influenza virus after step d).

2. The method of producing reassortant influenza virus according to claim 1, wherein the step d( comprises incubating the culture product obtained in step c) with antiserum containing the neutralizing antibody that binds to an antigenic protein of the second influenza virus strain.

3. The method of producing reassortant influenza virus according to claim 2, wherein the antiserum has final dilution factor of from 2 times to 1,000 times.

4. The method of producing reassortant influenza virus according to claim 2, wherein the antiserum comprises infected serum obtained from blood collected from a mammal infected with the second influenza virus strain.

5. The method of producing reassortant influenza virus according to claim 1, wherein step b) comprises infecting the host cell with the first influenza virus strain by bringing the first influenza virus strain into contact with the host cell at MOI (multiplicity of infection) of from $1\times10^{\times6}$ to 10.

6. The method of producing reassortant influenza virus according to claim 1, wherein step b) comprises infecting the host cell with the first influenza virus strain, and then infecting the host cell with the second influenza virus strain.

7. The method of producing reassortant influenza virus according to claim 1, wherein step e) comprises isolating, from reassortant influenza virus, reassortant influenza virus of interest.

8. The method of producing reassortant influenza virus according to claim 1, wherein the second influenza virus strain comprises influenza A virus subtype H1N1 or influenza A virus subtype H3N2.

9. The method of producing reassortant influenza virus according to claim 2, wherein step b) comprises infecting the host cell with the first influenza virus strain by bringing the first influenza virus strain into contact with the host cell at MOI (multiplicity of infection) of from $1\times10^{-6}$ to 10.

10. The method of producing reassortant influenza virus according to claim 2, wherein step b) comprises infecting the host cell with the first influenza virus strain, and then infecting the host cell with the second influenza virus strain.

11. The method of producing reassortant influenza virus according to claim 2, wherein step e) comprises isolating from reassortant influenza virus, reassortant influenza virus of interest.

12. The method of producing reassortant influenza virus according to claim 2, wherein the second influenza virus strain comprises influenza A virus subtype H1N1 or influenza A virus subtype H3N2.

* * * * *